United States Patent
Wang et al.

(10) Patent No.: US 11,260,084 B2
(45) Date of Patent: Mar. 1, 2022

(54) FEED ADDITIVE FORMULATION AND METHODS OF MAKING AND USING THE SAME

(71) Applicant: BioResource International, Inc., Durham, NC (US)

(72) Inventors: Jeng-Jie Wang, Apex, NC (US); Giles Shih, Durham, NC (US)

(73) Assignee: BioResource International, Inc., Durham, NC (US)

( * ) Notice: Subject to any disclaimer, the term of this patent is extended or adjusted under 35 U.S.C. 154(b) by 16 days.

(21) Appl. No.: 16/543,706

(22) Filed: Aug. 19, 2019

(65) Prior Publication Data

US 2019/0374585 A1 Dec. 12, 2019

Related U.S. Application Data

(63) Continuation of application No. PCT/US2018/021284, filed on Mar. 7, 2018.

(60) Provisional application No. 62/467,848, filed on Mar. 7, 2017.

(51) Int. Cl.

| | |
|---|---|
| *A61K 35/742* | (2015.01) |
| *A61P 31/04* | (2006.01) |
| *A61P 1/14* | (2006.01) |
| *A61P 33/02* | (2006.01) |
| *A61K 9/00* | (2006.01) |
| *A61K 38/47* | (2006.01) |
| *A61K 47/02* | (2006.01) |
| *A23K 10/18* | (2016.01) |
| *A23K 20/189* | (2016.01) |
| *A23K 20/24* | (2016.01) |
| *A23K 50/75* | (2016.01) |
| *A23K 50/30* | (2016.01) |
| *A61K 35/00* | (2006.01) |

(52) U.S. Cl.
CPC ............ *A61K 35/742* (2013.01); *A23K 10/18* (2016.05); *A23K 20/189* (2016.05); *A23K 20/24* (2016.05); *A23K 50/30* (2016.05); *A23K 50/75* (2016.05); *A61K 9/0056* (2013.01); *A61K 38/47* (2013.01); *A61K 47/02* (2013.01); *A61P 1/14* (2018.01); *A61P 31/04* (2018.01); *A61P 33/02* (2018.01); *C12Y 302/01008* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 4,908,220 A * | 3/1990 | Shih | A23J 1/10 426/61 |
| 4,959,311 A | 9/1990 | Shih et al. | |
| 5,612,055 A * | 3/1997 | Bedford | C12N 9/248 424/442 |
| 10,006,017 B2 * | 6/2018 | Hoff | A23K 40/20 |
| 10,695,384 B2 * | 6/2020 | Millan | A61K 35/741 |
| 2010/0143316 A1 * | 6/2010 | Hsieh | A23K 10/18 424/93.46 |
| 2014/0234279 A1 * | 8/2014 | Millan | A61P 1/04 424/93.41 |
| 2015/0290254 A1 | 10/2015 | Remus et al. | |

FOREIGN PATENT DOCUMENTS

| | | | | |
|---|---|---|---|---|
| JP | 2014507946 A | | 4/2014 | |
| WO | WO-2014020141 A1 * | | 2/2014 | ............. A23K 50/60 |

OTHER PUBLICATIONS

EPO, Extended European Search Report for corresponding EP Patent Application No. 18763771.5, dated Dec. 7, 2020, 15 pages.
Mengjia Zhou et al.: "Effects of Bacillus licheniformis on the growth performance and expression of lipid metabolism-related genes in broiler chickens challenged with Clostridium perfringens-i nd uced necrotic enteritis", Lipids in Health and Disease (2016) 15:48, 10 pages.
WIPO, International Preliminary Report on Patentability for International Patent Application No. PCT/US2018/021284 dated Sep. 10, 2019, 7 pages.
ISA/US, International Search Report and Written Opinion for International Patent Application No. PCT/US2018/021284, dated May 25, 2018.

* cited by examiner

*Primary Examiner* — Nghi V Nguyen
(74) *Attorney, Agent, or Firm* — NK Patent Law

(57) ABSTRACT

The presently disclosed subject matter relates to feed additive formulations for monogastric animal feed. Particularly, the disclosed formulations comprise an isolated xylanase enzyme and a *B. licheniformis* strain PWD-1. The feed additive formulations may further include *B. amyloliquefaciens* strain Ba-BPD1. The disclosed formulations are useful for addition to feeds for monogastric animals to synergistically improve the performance of the animals.

6 Claims, 13 Drawing Sheets

FEED ADDITIVE FORMULATION AND METHODS OF MAKING AND USING THE SAME

CROSS REFERENCE TO RELATED APPLICATIONS

This application is a continuation of International Patent Application No. PCT/US2018/021284, filed Mar. 7, 2018, which claims priority to U.S. Provisional Patent Application No. 62/467,848, filed Mar. 7, 2017, the entire contents of each of which are incorporated by reference herein.

FIELD OF INVENTION

The presently disclosed subject matter relates generally to a feed additive formulation and to methods of making and using the disclosed formulation.

BACKGROUND

For decades, animal production has depended on antibiotic growth promotors (AGPs) to maintain animal health and improve productivity. With the removal of AGPs from animal production in many countries, producers have attempted to use various feed additives, such as organic acids, enzymes, and probiotics with varying levels of efficacy and inconsistent results. Particularly, many enzyme and probiotic products currently used in the market are costly and have been proven to be unstable when used in industry feed and animal production processes. It would therefore be beneficial to provide novel combinations of enzymes and probiotics that significantly improve production performance characteristics of animals when added to animal feeds.

SUMMARY

In some embodiments, the presently disclosed subject matter is directed to a feed additive formulation for monogastric animal feeds. Particularly, the formulation comprises an isolated xylanase enzyme and a biologically pure culture of *Bacillus licheniformis* strain PWD-1 (Accession No. 53757) or a mutant having all of the identifying characteristics thereof. In some embodiments, the formulation further comprises a biologically pure culture of *Bacillus amyloliquefaciens* strain Ba-BPD1 (Accession No. DSM 21836) or a mutant having all the identifying characteristics thereof.

In some embodiments, the presently disclosed subject matter is directed to a feed composition for monogastric animals comprising an isolated xylanase enzyme and a biologically pure culture of *Bacillus licheniformis* strain PWD-1 (Accession No. 53757) or a mutant having all of the identifying characteristics thereof. In some embodiments, the feed composition further comprises a biologically pure culture of *Bacillus amyloliquefaciens* strain Ba-BPD1 (Accession No. DSM 21836) or a mutant having all the identifying characteristics thereof.

In some embodiments, the presently disclosed subject matter is directed to a method of increasing the performance of a monogastric animal. The method comprises administering to the animal an effective amount of a feed composition comprising a xylanase enzyme and a biologically pure culture of *Bacillus licheniformis* strain PWD-1 (Accession No. 53757) or a mutant having all the identifying characteristics thereof. In some embodiments of the method, the feed composition further comprises a biologically pure culture of *Bacillus amyloliquefaciens* strain Ba-BPD1 (Accession No. DSM 21836) or a mutant having all the identifying characteristics thereof.

In some embodiments, the presently disclosed subject matter is directed to a method of preparing a feed composition for monogastric animals. Particularly, the method comprises adding to the feed composition a formulation comprising a xylanase enzyme and a biologically pure culture of *Bacillus licheniformis* strain PWD-1 (Accession No. 53757) or a mutant having all the identifying characteristics thereof. In some embodiments of the method, the formulation further comprises a biologically pure culture of *Bacillus amyloliquefaciens* strain Ba-BPD1 (Accession No. DSM 21836) or a mutant having all the identifying characteristics thereof.

DETAILED DESCRIPTION

Figure 1A:
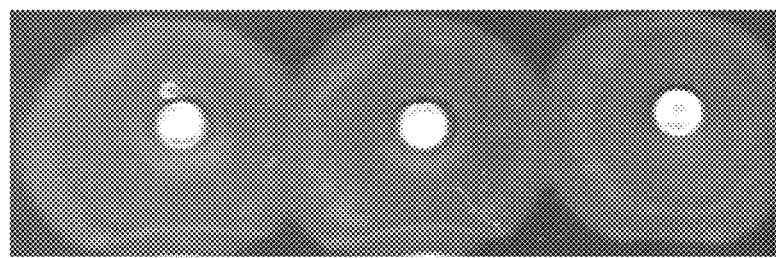
FIG. 1a is a photograph of 3 agar diffusion assays showing the interaction between *Listeria innocua* and *B. licheniformis* strain PWD-1.

The presently disclosed subject matter now will be described more fully hereinafter with reference to the accompanying Figures, in which some (but not all) embodiments are shown. Many modifications and other embodiments of the presently disclosed subject matter set forth herein will come to mind to one skilled in the art having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Unless otherwise defined, all technical terms used herein have the same meaning as commonly understood by one of ordinary skill in the art to which this disclosure belongs.

Following long-standing patent law convention, the terms "a," "an," and "the" refer to one or more when used in this application, including the claims. Thus, for example, reference to "a protein" includes a plurality of proteins, unless the context clearly is to the contrary.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Throughout this specification and the claims, the terms "comprise," "comprises," and "comprising" are used in a non-exclusive sense, except where the context requires otherwise. Likewise, the terms "include" and "have" and grammatical variants are intended to be non-limiting, such that recitation of items in a list is not to the exclusion of other like items that can be substituted or added to the listed items.

The presently disclosed subject matter relates to feed additive formulations for use with monogastric animal feed. Particularly, the disclosed formulations comprise an isolated xylanase enzyme and at least one microbial probiotic strain *Bacillus licheniformis* PWD-1 (Accession No. 53757), or a mutant thereof having all the identifying characteristics thereof. The disclosed formulation can be added to animal feeds, resulting in unexpected synergistically improved animal characteristics as set forth in more detail herein below.

Thus, the disclosed feed additive formulation comprises an isolated xylanase enzyme as an essential component. The term "xylanase" as used herein refers to a class of enzymes that degrade the linear polysaccharide beta-1,4-xylan into xylose, thus breaking down hemicellulose, one of the major components of plant cell walls. In some embodiments, the xylanase is an endo-1,4-beta-xylanase. The term "isolated" as used herein refers to an enzyme that is substantially pure (i.e., free of contaminating molecules).

Xylanase enzymes suitable for use in the disclosed formulation can be produced using methods well known in the art. For example, in some embodiments, the xylanase can be produced by solid or submerged culture, including batch, fed-batch, and continuous-flow processes. Alternatively or in addition, the xylanase can be any commercially available xylanase. The xylanase can be provided as a liquid or a dry (powder) preparation.

The xylanase can be obtained from any suitable source known or used in the art, such as from a bacterium selected from *Bacillus*, *Streptomyces*, *Clostridium*, *Thermonospora*, *Trichoderma*, *Thermomyces*, *Aspergillus*, *Penicillium*, *Microtetra-spora*, *Ruminococcus*, and the like. Alternatively or in addition, the xylanase can be obtained from a fungus selected from *Trichoderma*, *Aspergillus*, *Humicola*, *Neocallimastix*, and the like.

In some embodiments, the xylanase is stable and active at a pH and temperature at or close to the conditions found in the gastrointestinal tract of an animal.

The disclosed formulation further comprises a biologically pure culture of the microbial *Bacillus licheniformis* strain PWD-1 (Accession No. 53757) or a mutant having all of the identifying characteristics thereof. *Bacillus licheniformis* strain PWD-1 is described in U.S. Pat. Nos. 4,908,220 and 4,959,311, the entire disclosures of which are hereby incorporated by reference. In some embodiments, the disclosed formulation further comprises a biologically pure culture of *Bacillus amyloliquefaciens* strain Ba-BPD1 (Accession No. DSM 21836) or a mutant having all of the identifying characteristics thereof. *Bacillus amyloliquefaciens* strain Ba-BPD1 is described in U.S. Patent Application Publication No. 2010/0143316, the entire content of which is hereby incorporated by reference.

*Bacillus licheniformis* strain PWD-1 was deposited with the American Type Culture Collection in accordance with the Budapest Treaty on Mar. 23, 1988, and was assigned ATCC Accession No. 53757. *Bacillus amyloliquefaciens* Ba-BPDI was deposited in the Deutsche Sammlung von Mikroorganism and Zellkulturen GmbH (DSMZ), Inhoffenstr. 7B, D-38124 Braunschweig, Germany, on Sep. 11, 2008, under the rules of the Budapest Treaty, and the deposit number was DSM 21836.

The term "biologically pure culture" refers to a culture that is physically separated from microorganisms of different characteristics. As used herein, the phrase "a biologically pure culture of a bacterial strain" refers to one or a combination of: spores of the biologically pure fermentation culture of a bacterial strain, vegetative cells of the biologically pure fermentation culture of a bacterial strain, one or more products of the biologically pure fermentation culture of a bacterial strain, a culture solid of the biologically pure fermentation culture of a bacterial strain, a culture supernatant of the biologically pure fermentation culture of a bacterial strain, an extract of the biologically pure fermentation culture of the bacterial strain, and one or more metabolites of the biologically pure fermentation culture of a bacterial strain.

The term "mutant" as used herein refers to a genetic variant derived from the parent strain (i.e., *Bacillus licheniformis* strain PWD-1 or *Bacillus amyloliquefaciens* strain Ba-BPD1). In some embodiments, the mutant performs as well as or better than the parent strain (e.g., maintains or improves the growth of an animal as well as or better than the parent strain).

The *Bacillus licheniformis* and/or *Bacillus amyloliquefaciens* strains can be obtained from research labs or from culture collections. A biologically pure culture can be produced using methods well known in the art, such as by cultivation in a culture-specific medium using aseptic technique and under appropriate conditions (i.e., pH, temperature, oxygen level, and the like).

Figure 1B:
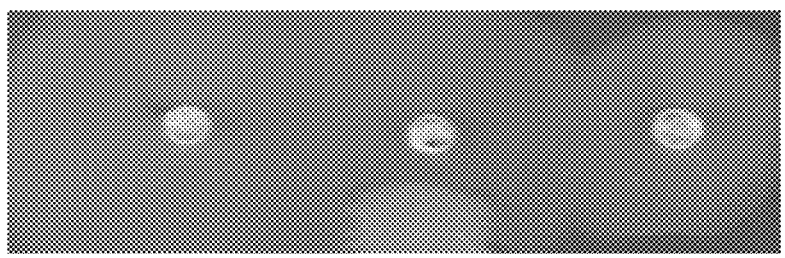
FIG. 1b is a photograph of 3 agar diffusion assays showing the interaction between *Salmonella enteria* and *B. licheniformis* strain PWD-1.
Figure 2A:
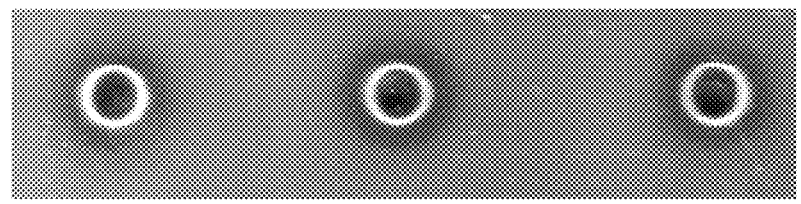
FIG. 2a is a photograph of 3 agar diffusion assays showing the interaction between *E. coli* and *B. amyloliquefaciens* strain Ba-BPD1.
Figure 2B:
FIG. 2b is a photograph of 3 agar diffusion assays showing the interaction between *Salmonella enterica* and *B. amyloliquefaciens* strain Ba-BPD1.
Figure 2C:
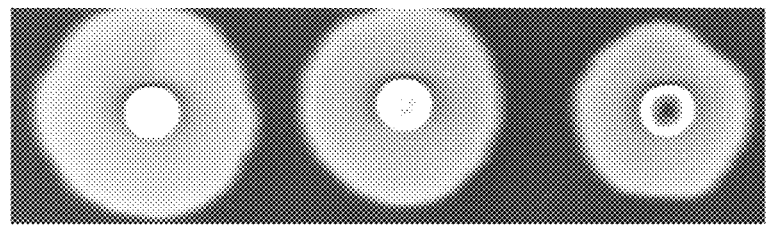
FIG. 2c is a photograph of 3 agar diffusion assays showing the interaction between *Listeria innocua* and *B. amyloliquefaciens* strain Ba-BPD1.

EXAMPLES 1 and 2 of the present disclosure show that the *B. licheniformis* strain PWD-1 and the *B. amyloliquefaciens* strain Ba-BPD1 inhibit the growth of human and animal pathogens including *Listeria innocua*, a *E. coli* and *Salmonella enteric*. FIGS. 1a and 1b illustrate that *B. licheniformis* strain PWD-1 overgrows *Listeria innocua* and *Salmonella enteria*, respectively. FIGS. 2a and 2b illustrate that *B. amyloliquefaciens* strain Ba-BPD1 inhibits the growth of *E. coli* and *Salmonella enterica*, respectively. FIG. 2c illustrates that *B. amyloliquefaciens* strain Ba-BPD1 outgrows *Listeria innocua*.

Figure 3A:
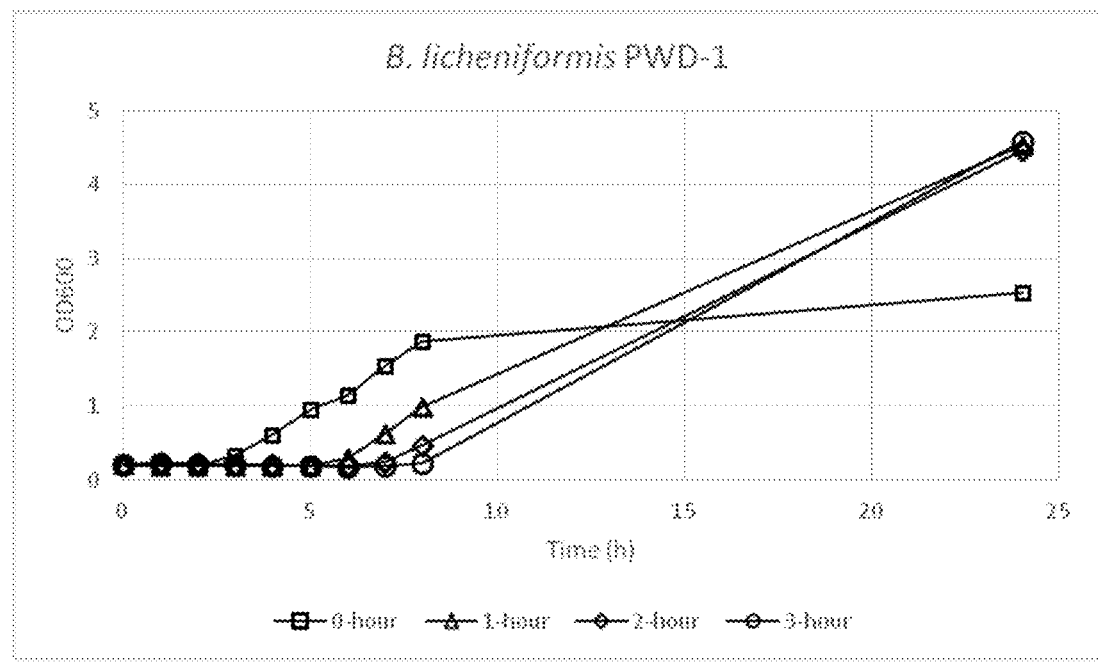
FIG. 3a is a line graph illustrating the growth of *B. licheniformis* strain PWD-1 over 24 hours after incubation at pH 3.0 for 0, 1, 2, or 3 hours.
Figure 3B:
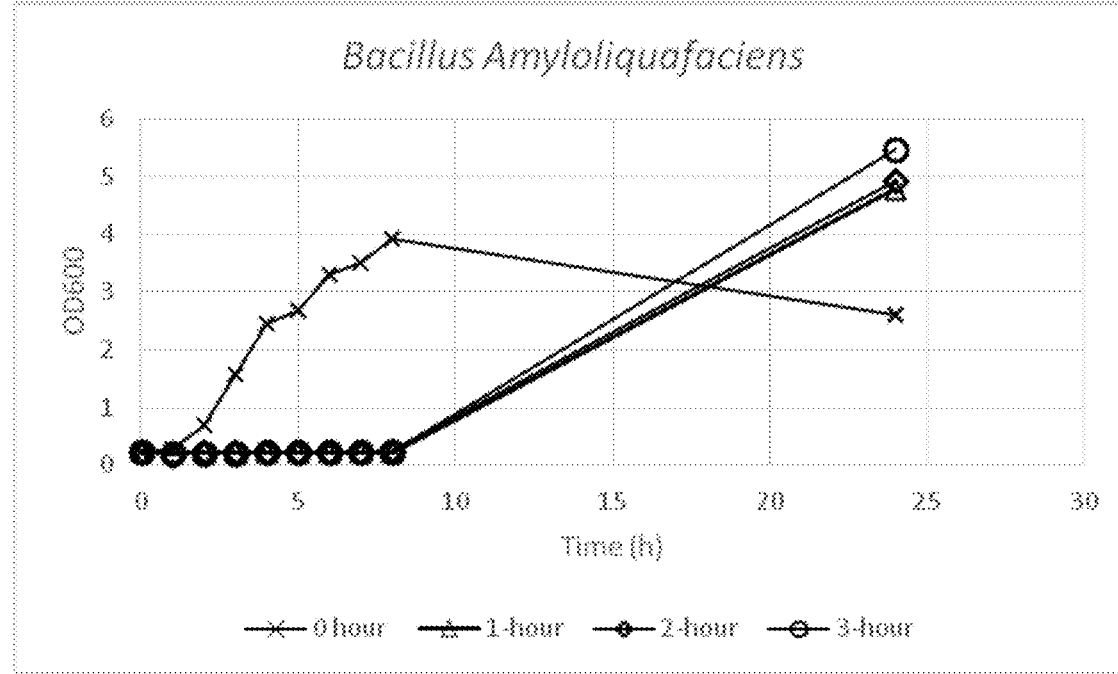
FIG. 3b is a line graph illustrating the growth of *B. amyloliquefaciens* strain Ba-BPD1 over 24 hours after incubation at pH 3.0 for 0, 1, 2, or 3 hours.

EXAMPLE 3 of the present disclosure shows that the *B. licheniformis* strain PWD-1 and the *B. amyloliquefaciens* strain Ba-BPD1 are resistant to acidic environments which is an important feature of probiotic microorganisms due to exposure of the microbial strain to the harsh acidic conditions present in the gut of an animal before passing into the intestine. As shown in FIG. 3a, the exposure of *B. licheniformis* strain PWD-1 to an acidic environment delayed growth for 3 hours compared to neutral media. It was also observed that *B. licheniformis* strain PWD-1 exposed to the acidic environment for 1, 2, and 3 hours was able to recover and assume growth. As shown in FIG. 3b, *B. amyloliquefaciens* strain Ba-BPD1 was also able to recover from the acid exposure, although slower than observed for the *B. licheniformis* strain.

Figure 4A:
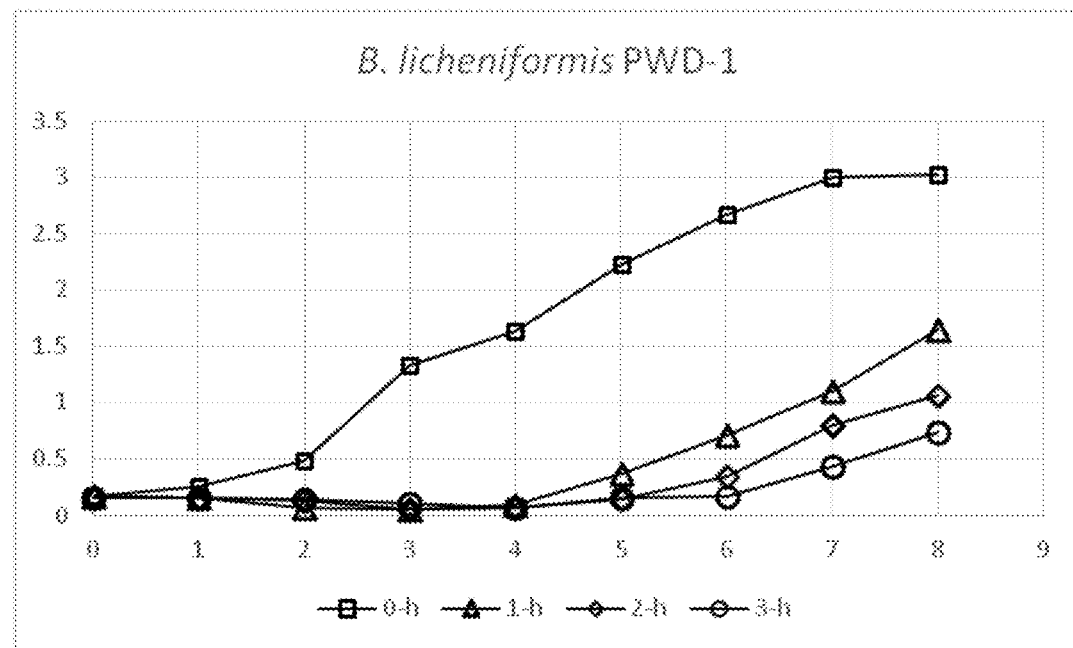
FIG. 4a is a line graph illustrating the growth of *B. licheniformis* strain PWD-1 over 8 hours with 0, 1, 2, or 3 hour initial exposure to Ox gall in LB media.
Figure 4B:
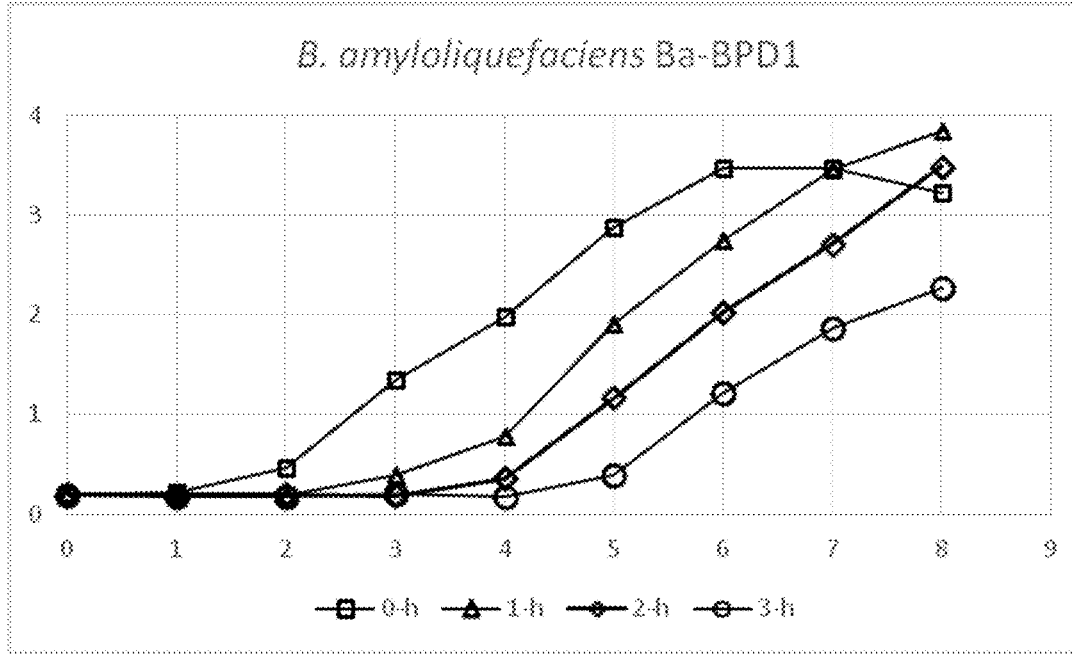
FIG. 4b is a line graph illustrating the growth of *B. amyloliquefaciens* strain Ba-BPD1 over 8 hours with 0, 1, 2, or 3 hour initial exposure to Ox gall in LB media.

Similarly, the survival of probiotic microorganisms in a gastric environment includes not only a low pH environment, but also enzymes secreted into the gastrointestinal tract in the bile. EXAMPLE 4 of the present disclosure shows that the *B. licheniformis* strain PWD-1 and the *B. amyloliquefaciens* strain Ba-BPD1 were able to recover after exposure to Ox gall (cow gall mixed with alcohol) that has traditionally been used as a representation of the gastric environment. FIGS. 4a and 4b illustrate that both *B. licheniformis* strain PWD-1 and *B. amyloliquefaciens* strain Ba-BPD1 were able to recover after up to 3 hours of exposure to Ox gall in LB media.

Figure 5:
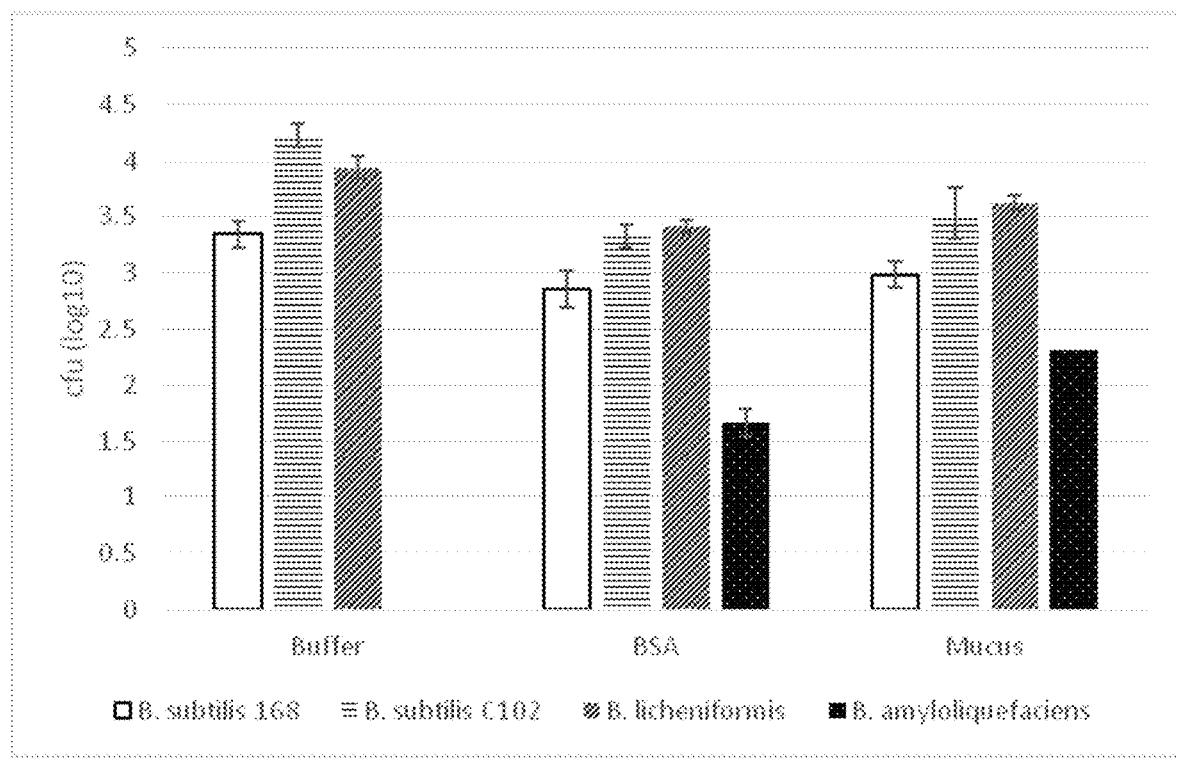
FIG. 5 is a bar graph illustrating the growth of *B. licheniformis* strain PWD-1, *B. amyloliquefaciens* strain Ba-BPD1, *B. subtilis* strain 168, and *B. subtilis* strain C102 in the presence of buffer, bovine serum albumin, and swine mucus.

Attachment of probiotic strains to intestinal mucus is desirable because it limits access of pathogens to the mucus lining. EXAMPLE 5 of the present disclosure shows that the *B. licheniformis* strain PWD-1 and *B. amyloliquefaciens* strain Ba-BPD1 have the ability to attach to swine mucus. FIG. 5 shows that *B. licheniformis* strain PWD-1 adheres to swine mucus at comparable levels to control strain *B. subtilis* strain C102.

EXAMPLE 6 of the present disclosure describes a study showing the effects of addition of xylanase and *B. licheniformis* Strain PWD-1 to the diet of commercial broiler poultry. The birds were fed a feed composition containing $10^6$ CFU/g *B. licheniformis* Strain PWD-1 and 15 U/g xylanase (Table 1). The trial environment included mild stress such as bacteria/cocci challenge through built up litter bedding as well as severe stress. Specifically, birds were challenged with multiple pathogens on the $1^{st}$, $7^{th}$, and $10^{th}$ day (post hatching), including *Clostridium perfringens* at a bacterial dose (cells per bird) of $>10^7$, *Eimeria acervulina* at $10^4$ cells per bird, and *Eimeria maxima* at $10^3$ cells per bird. Intestinal lesion scores were measured at 14, 21, and 42 days of age. Lower scores are desired. Each diet was corn/soy-based, but had 100 kcal/kg less metabolizable energy (ME) compared to a standard broiler diet (Table 2). Group BWG (body weight gain) and FCR (feed conversion ratio) for various periods were calculated based on BW (body weight) and FI (food intake) (Table 3).

The results of the lesion score analysis from this study are shown below in Table 4 and in FIG. 6.

TABLE 4

Intestinal lesion scores in broilers challenged with *Clostridium perfringens*, *Eimeria acervulina*, and *Eimeria maxima* and fed a feed composition containing $10^6$ CFU/g *B. licheniformis* Strain PWD-1 and 15 U/g xylanase.

| Age (Days) | Control | Pro B | Xylanase | Combined Pro B/ Xylanase | Reduction Pro B alone | Reduction Xylanase alone | Reduction Pro B/ Xylanase combined | Calculated Additive Reduction Pro B and Xylanase Separately |
|---|---|---|---|---|---|---|---|---|
| 14 | 1.63 | 1.00 | 0.50 | 0.25 | −(0.63) | −(1.13) | −(1.38) | −(1.73) |
| 21 | 1.28 | 1.03 | 0.94 | 0.38 | −(0.25) | −(0.34) | −(0.90*) | −(0.59) |
| 42 | 1.21 | 1.06 | 1.03 | 0.43 | −(0.15) | −(0.18) | −(0.78*) | −(0.33) |

*indicates a strong synergistic effect.

Figure 6:
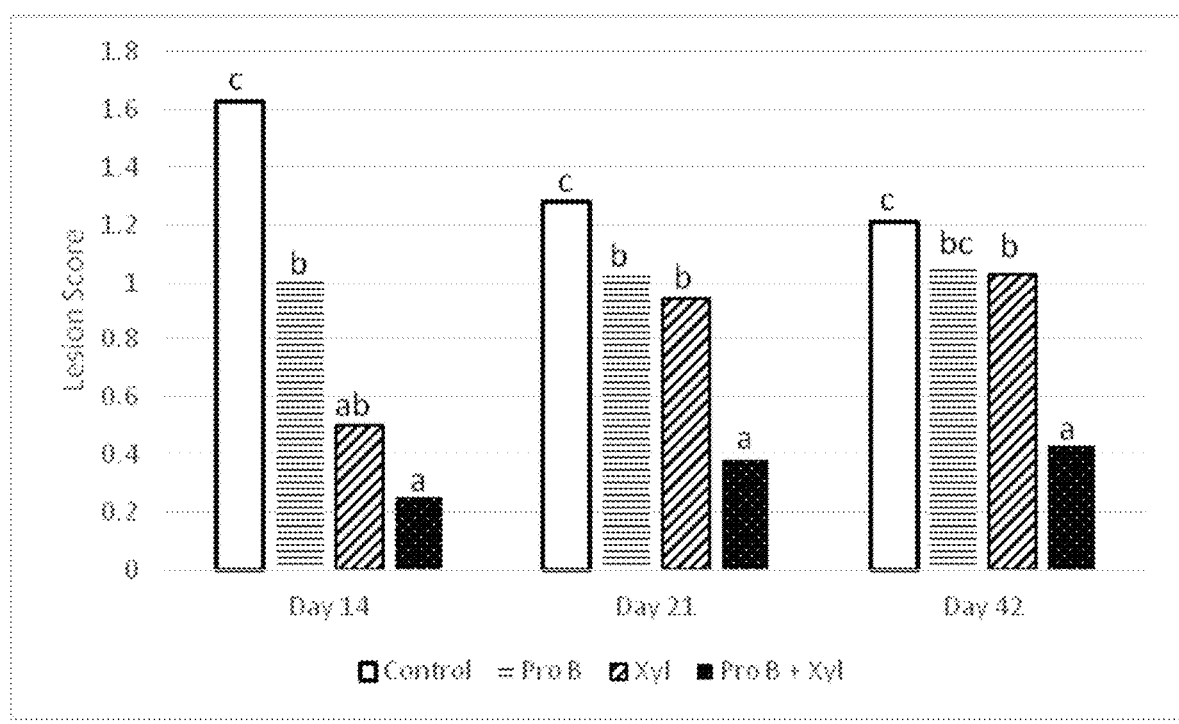
FIG. 6 is a series of bar graphs illustrating the lesion scores from 14-day, 21-day, and 42-day old broilers fed animal feed supplemented with *B. licheniformis* strain PWD-1, xylanase, both *B. licheniformis* strain PWD-1 and xylanase, and control.

The data in Table 4 and FIG. 6 show that the combination of the xylanase and the *B. licheniformis* Strain PWD-1 had an unexpectedly beneficial effect on lowering intestinal lesions in the pathogen challenged birds. Specifically, the reduction in the lesion scores at 21 and 42 days for the birds fed the feed containing both xylanase and *B. licheniformis* Strain PWD-1 of 0.90 and 0.78, respectively, was significantly greater than the additive effect of each of the components alone (i.e., 0.59 and 0.33, respectively). At the 42 day time point, the improvement due to the combination feed was pronounced at greater than twice that of the additive reduction (i.e., a 0.78 versus 0.33 reduction). Thus, the combination of the xylanase and the *B. licheniformis* Strain PWD-1 shows synergistic improvements in animal health.

Figure 7A:
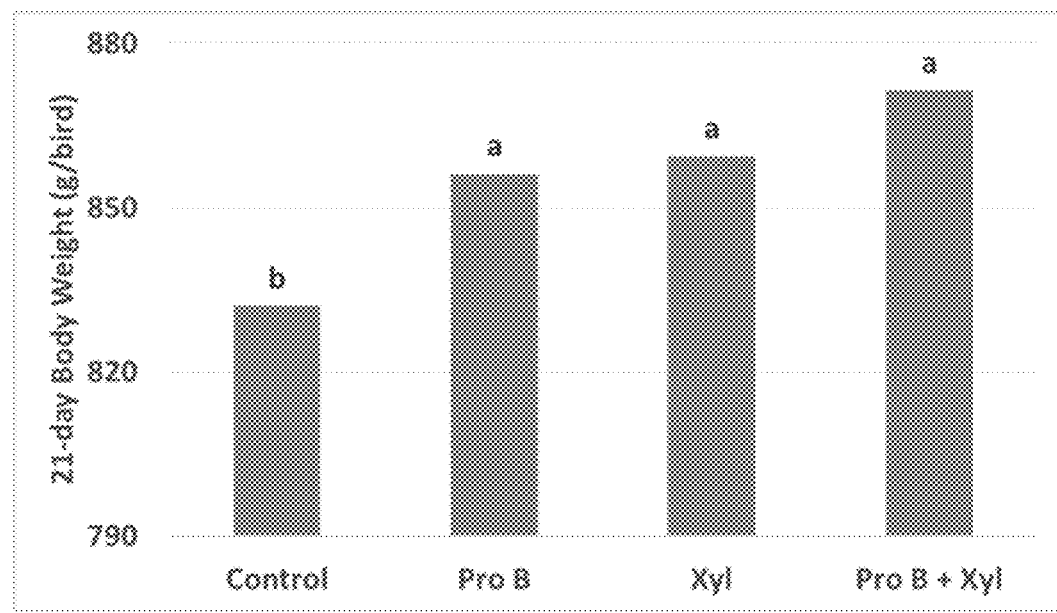
FIG. 7a is a bar graph illustrating the 21-day body weights of broilers fed animal feed supplemented with *B. licheniformis* strain PWD-1, xylanase, both *B. licheniformis* strain PWD-1 and xylanase, and control.
Figure 7B:
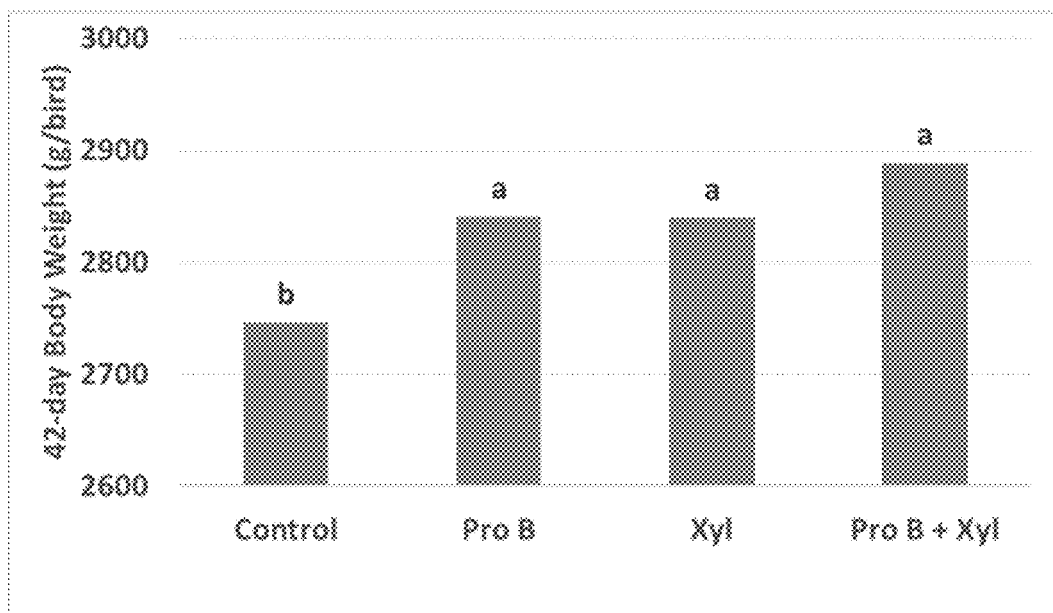
FIG. 7b is a bar graph illustrating the 42-day body weights of broilers fed animal feed supplemented with *B. licheniformis* strain PWD-1, xylanase, both *B. licheniformis* strain PWD-1 and xylanase, and control.

EXAMPLE 6 of the present disclosure also describes the effects on body weight (BW), feed conversion rate (FCR), and *Salmonella* incidence when xylanase and *B. licheniformis* Strain PWD-1 are added to the diet of commercial broiler poultry. FIGS. 7a and 7b illustrate that xylanase and *B. licheniformis* strain PWD-1 significantly ($p<0.05$) improved BW of the birds at 21-days and 42-days of age. In addition, the improvement of the xylanase and *B. licheniformis* strain PWD-1 combination was shown to be greater than either component alone.

Figure 8A:
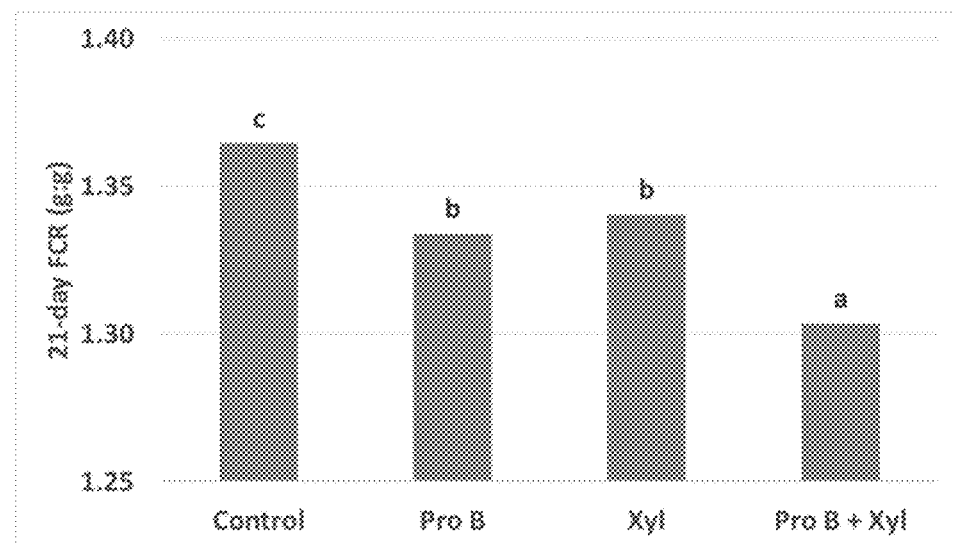
FIG. 8a is a bar graph illustrating the feed conversion rate (FCR) of 21-day broilers fed animal feed supplemented with *B. licheniformis* strain PWD-1, xylanase, both *B. licheniformis* strain PWD-1 and xylanase, and control.
Figure 8B:
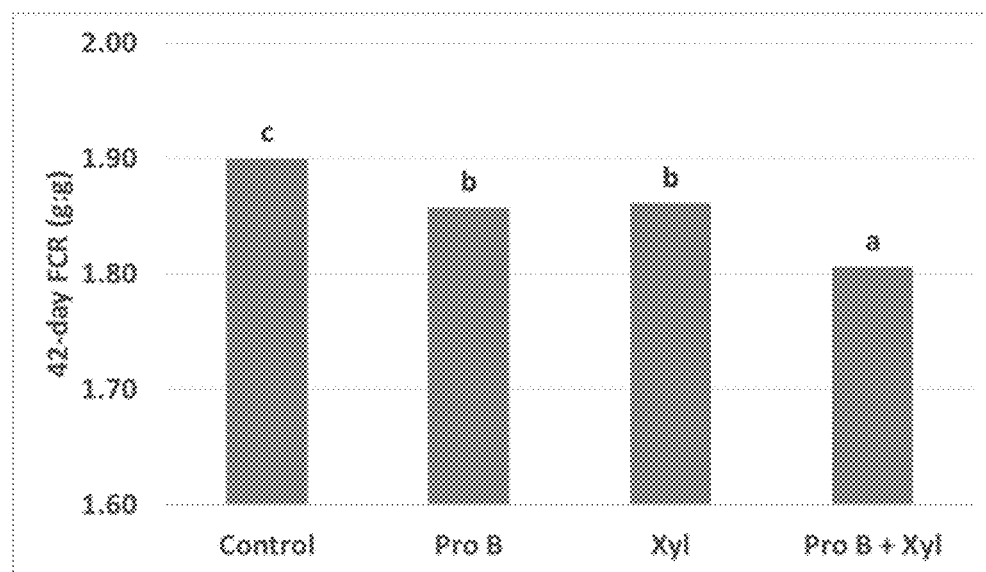
FIG. 8b is a bar graph illustrating the feed conversion rate (FCR) of 42-day broilers fed animal feed supplemented with *B. licheniformis* strain PWD-1, xylanase, both *B. licheniformis* strain PWD-1 and xylanase, and control.

The results further illustrate that xylanase and *B. licheniformis* strain PWD-1 significantly ($p<0.05$) improved FCR at 21-days and 42-days of age (FIGS. 8a and 8b). In addition, the improvement of the xylanase and *B. licheniformis* strain PWD-1 combination was greater than either component alone, as shown in FIGS. 8a and 8b.

Figure 9A:
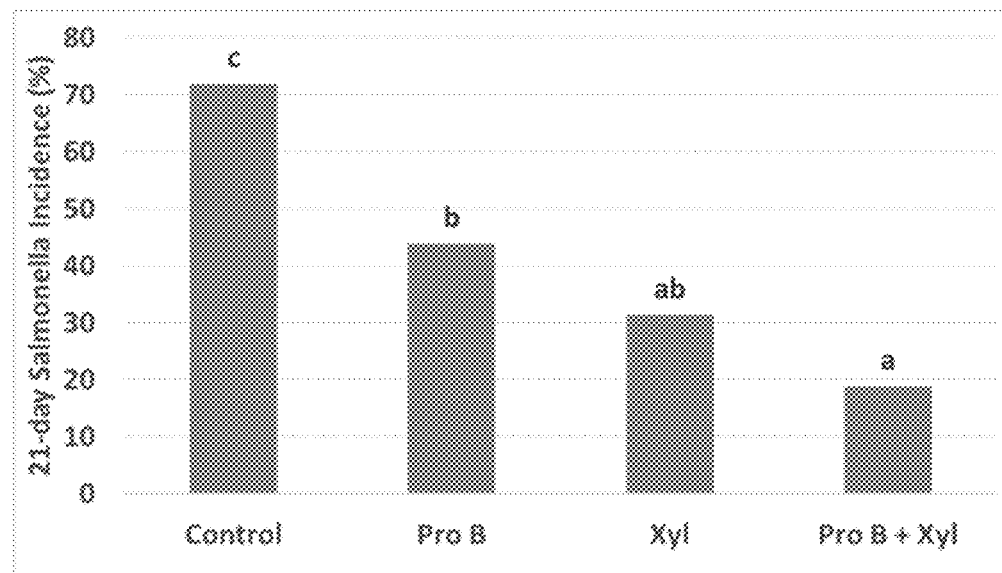
FIG. 9a is a bar graph illustrating the *Salmonella* incidence (%) of 21-day and old broilers fed animal feed supplemented with *B. licheniformis* strain PWD-1, xylanase, both *B. licheniformis* strain PWD-1 and xylanase, and control.
Figure 9B:
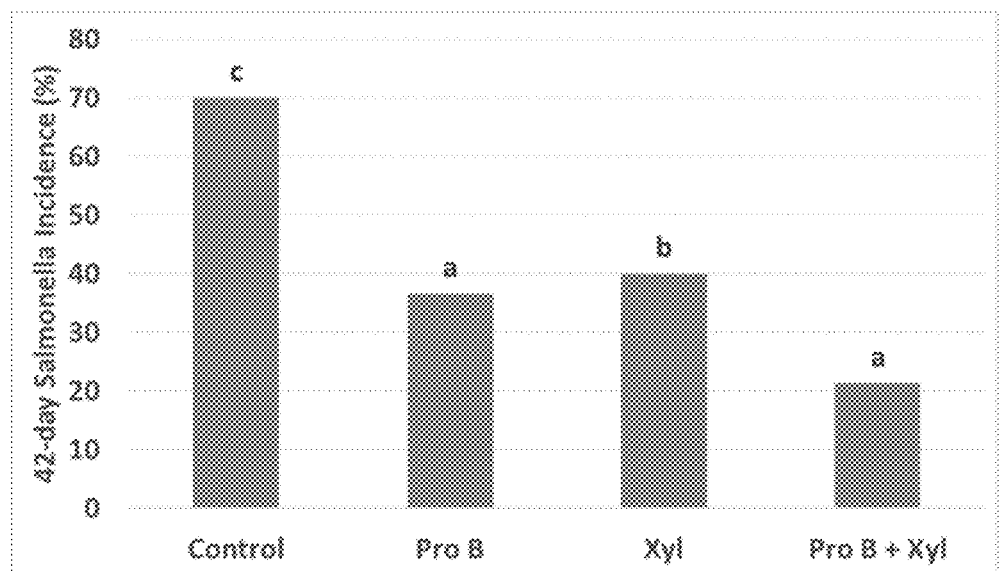
FIG. 9b is a bar graph illustrating the *Salmonella* incidence (%) of 42-day old broilers fed animal feed supplemented with *B. licheniformis* strain PWD-1, xylanase, both *B. licheniformis* strain PWD-1 and xylanase, and control.

FIGS. 9a and 9b illustrate that xylanase and *B. licheniformis* strain PWD-1 significantly ($p<0.05$) reduced *Salmonella* incidence at 21-days and 42-days of age. In addition, the improvement of the xylanase and *B. licheniformis* strain PWD-1 combination was greater than either component alone.

Xylanase combined with *Bacillus licheniformis* strain PWD-1, when added to a corn/soy diet, can significantly improve broiler growth performance under *Clostridium perfringens* and multiple *Eimeria* species challenges.

EXAMPLE 7 of the present disclosure describes the effects of addition of xylanase, *B. licheniformis* strain PWD-1, and *B. amyloliquefaciens* strain Ba-BPD1 to the diet of commercial broilers. The broiler feed contained xylanase at a concentration of 15 units/gram feed and the concentration of each of the *B. licheniformis* and *B. amyloliquefaciens* strains ranged from $10^4$ to $10^6$ (Table 5).

Figure 10:
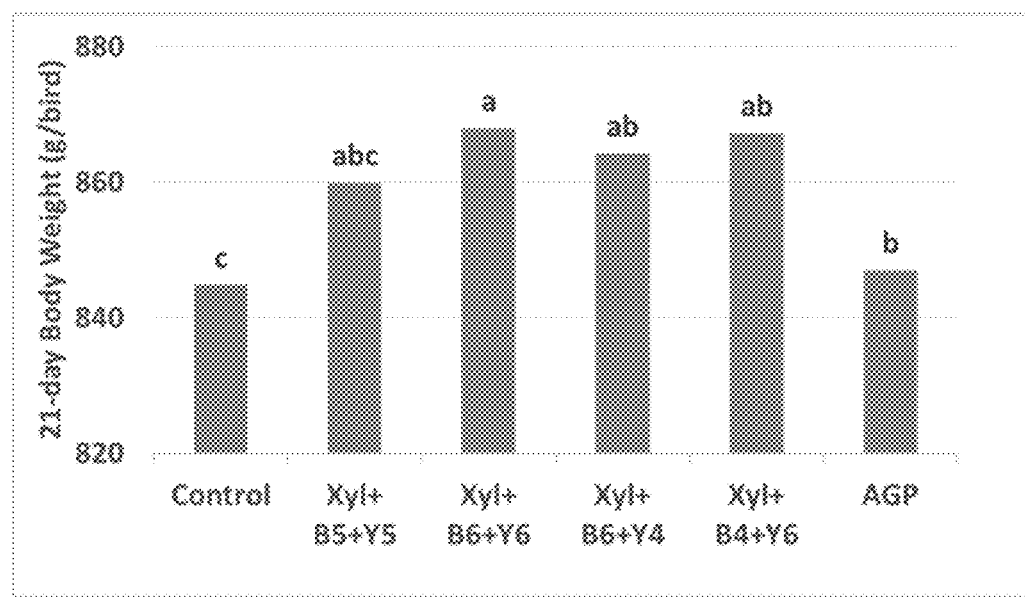
FIG. 10 is a bar graph illustrating the body weight of 21-day broilers fed animal feed supplemented with antibiotic growth promoter (AGP), xylanase+*B. licheniformis* strain PWD-1+*B. amyloliquefaciens* strain Ba-BPD1 at varying concentrations, and control.

As shown in FIG. 10, supplementing feed with xylanase and *Bacillus* strains (*Bacillus licheniformis* strain PWD-1 and *Bacillus amyloliquefaciens* strain Ba-BPD1) at $2\times10^5$ CFU/g of feed or higher significantly ($p<0.05$) improved body weight at 21-days of age.

Figure 11A:
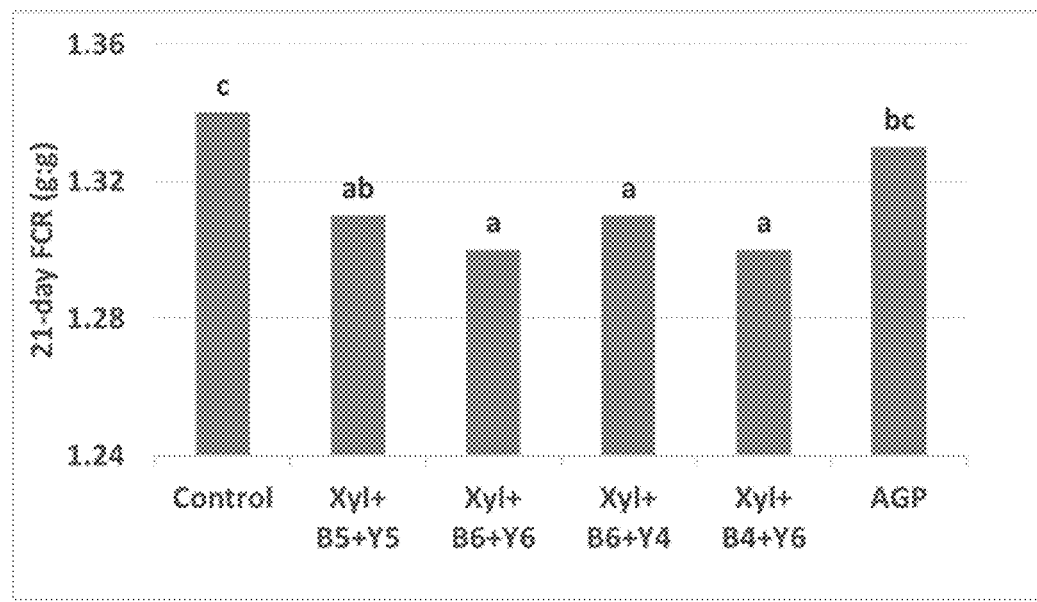
FIG. 11a is a bar graph illustrating the feed conversion rates of 21-day broilers fed animal feed supplemented with AGP, xylanase+*B. licheniformis* strain PWD-1+*B. amyloliquefaciens* strain Ba-BPD1 at varying concentrations, and control.
Figure 11B:
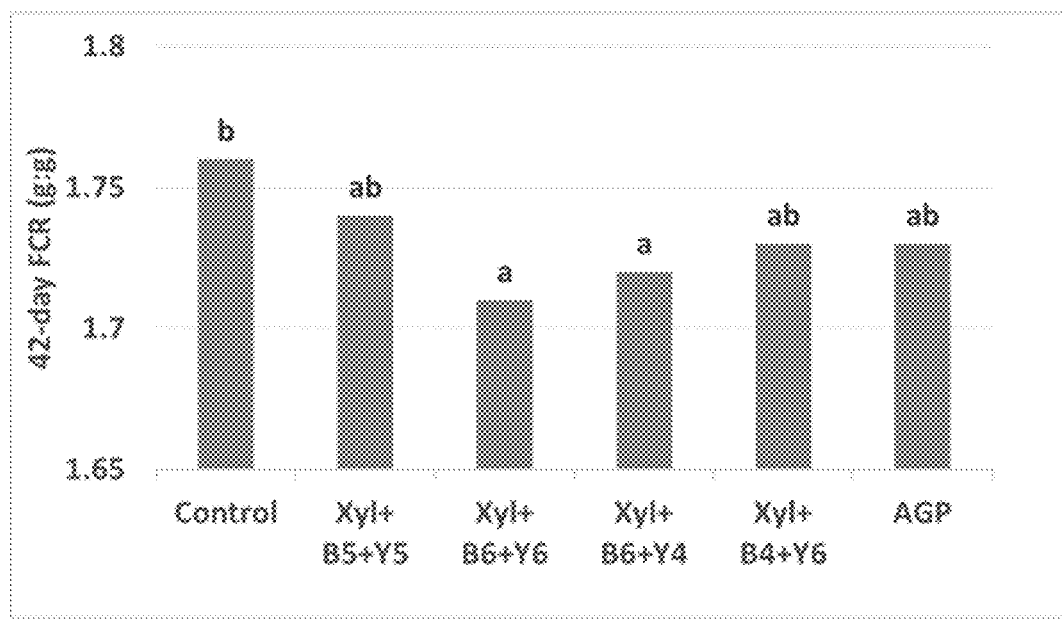
FIG. 11b is a bar graph illustrating the feed conversion rates of 42-day broilers fed animal feed supplemented with AGP, xylanase+*B. licheniformis* strain PWD-1+*B. amyloliquefaciens* strain Ba-BPD1 at varying concentrations, and control.

As shown in FIGS. 11a and 11b, supplementing feed with xylanase and *Bacillus* strains (*Bacillus licheniformis* strain PWD-1 and *Bacillus amyloliquefaciens* strain Ba-BPD1) at $2\times10^5$ CFU/g of feed or higher significantly ($p<0.05$) improved FCR at 21-days and 42-days of age.

Figure 12A:
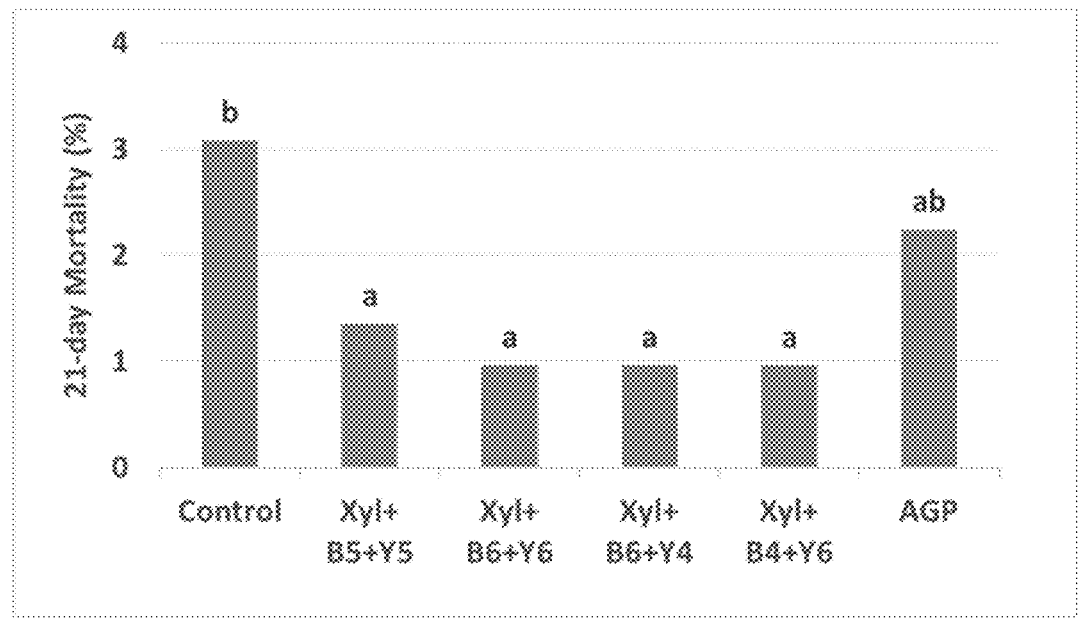
FIG. 12a is a bar graph illustrating the percent mortality of 21-day old broilers fed animal feed supplemented with AGP, xylanase+*B. licheniformis* strain PWD-1+*B. amyloliquefaciens* strain Ba-BPD1 at varying concentrations, and control.
Figure 12B:
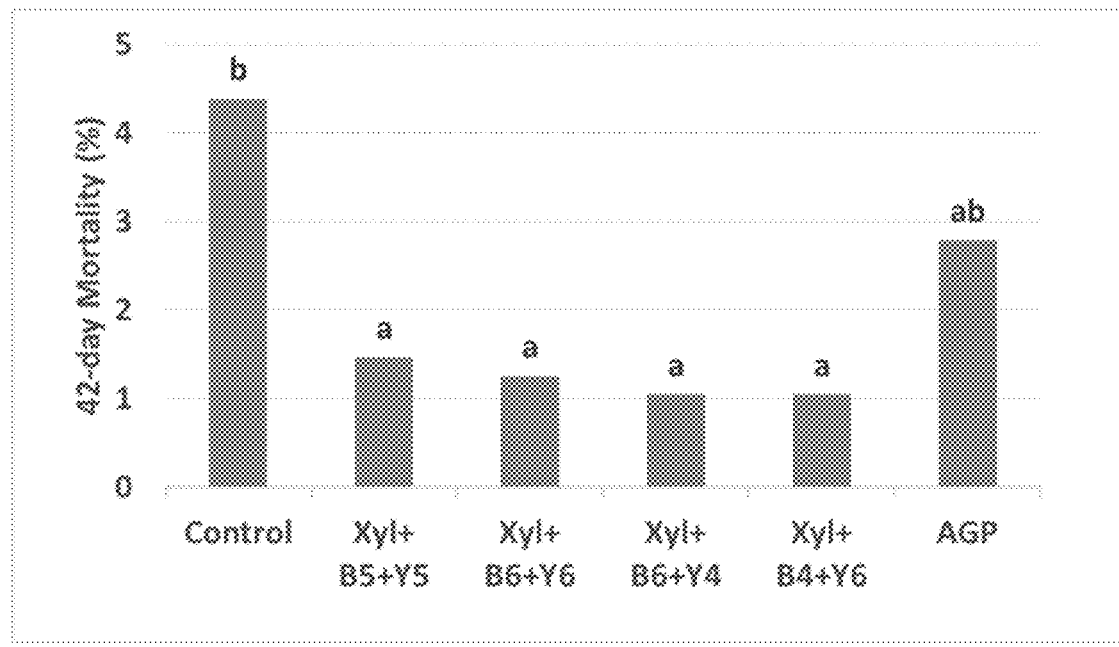
FIG. 12b is a bar graph illustrating the percent mortality of 42-day old broilers fed animal feed supplemented with AGP, xylanase+*B. licheniformis* strain PWD-1+*B. amyloliquefaciens* strain Ba-BPD1 at varying concentrations, and control.

Further, FIGS. 12a and 12b illustrate that supplementing feed with xylanase and *Bacillus licheniformis* strain PWD-1 and *Bacillus amyloliquefaciens* strain Ba-BPD1 at $2\times10^5$ CFU/g of feed or higher significantly ($p<0.05$) significantly reduced mortality of the birds at 21-days and 42-days of age (mortality was reduced by 80% on average at 42 days). In contrast, AGP (antibiotic BMD (bacitracin methylene disalicylate)) inclusion did not significantly improve mortality from the control.

Xylanase combined with *Bacillus licheniformis* strain PWD-1 and *Bacillus amyloliquefaciens* strain Ba-BPD1, when added to a corn/soy diet, can significantly improve broiler growth performance under *Clostridium perfringens* and multiple *Eimeria* species challenges.

EXAMPLE 8 of the present disclosure describes a study to evaluate the efficacy of a combination of xylanase (10 U/g feed), *B. licheniformis* strain PWD-1 ($1\times10^5$ CFU/g feed), and *B. amyloliquefaciens* strain Ba-BPD1 ($5\times10^5$ CFU/g feed) referred to as "Xyl+B+Y", to minimize the severity of gut lesions and improve overall livability of broiler chickens fed standard corn-soy diets and reared under severe coccidiosis challenge conditions. In the study chicks were twice challenged with a live vaccine containing the live oocysts of highly-immunogenic, coccidiostat-sensitive strains of *Eimeria acervulina, Eimeria maxima* and *Eimeria tenella* by oral gavage and the Xyl+B+Y combination was compared to salinomycin sodium which is referred to as "Coccidiostat" in FIG. 13.

At 7 days post-challenge (14 days of age), Xyl+B+Y alone reduced upper-tract lesion scores by 36%, relative to the challenged control (data not shown). At 14 days post-challenge, Xyl+B+Y alone reduced mid-tract lesion scores by 50%, compared to the challenged control (data not shown). The data shown in FIG. 13 demonstrate that mortality was significantly reduced ($P<0.02$) in the Xyl+B+Y treatment by 87%, compared to the challenged control. Comparatively the Coccidiostat treatment only reduced mortality by 25%. At 28 days, feed conversion ratio was reduced in the Xyl+B+Y treatment by 7 points, versus the challenged control (data not shown).

The combination of xylanase, *B. licheniformis* strain PWD-1, and *B. amyloliquefaciens* strain Ba-BPD1 can be more effective than coccidiostat alone at minimizing mortality of birds suffering severe *Eimeria* infections.

Thus, feed additive formulations for addition to feed compositions for monogastric animals are provided herein. The feed additive formulations are provided to add to feed compositions to improve the health and/or performance of monogastric animals such as, for example, poulty and swine. The increase in performance includes one or a combination of: increased average daily weight gain, increased total weight gain, improved feed conversion ratio, reduced lesion score, reduced mortality, reduced disease, or decreased pathogen incidence. The pathogens include, but are not limited to one or a combination of *Clostridium perfringens, Eimeria* spp., *Eimeria acervulina, Eimeria maxima, Eimeria tenella, Salmonella,* or Coccidiosis-inducing parasites. In one embodiment, the animal is poultry and the increase in performance comprises reduced lesion score resulting from one or a combination of *Clostridium perfringens* or *Eimeria* spp.

In one embodiment, a feed additive formulation for monogastric animal feed is provided comprising an isolated xylanase enzyme and a biologically pure culture of a *Bacillus licheniformis* strain PWD-1 (Accession No. 53757), or a mutant thereof having all the identifying characteristics thereof. The feed additive formulation may further comprise a biologically pure culture of a *Bacillus amyloliquefaciens* strain Ba-BPD1 (Accession No. DSM 21836), or a mutant thereof having all the identifying characteristics thereof.

In one embodiment, a feed composition for monogastric animals is provided that comprises the disclosed feed additive formulations.

In one embodiment, a method of preparing a feed composition for monogastric animals is provided, comprising adding to a feed composition a formulation comprising a xylanase enzyme and a biologically pure culture of a *Bacillus licheniformis* strain PWD-1 (Accession No. 53757), or a mutant thereof having all the identifying characteristics thereof. In the method, the formulation may further comprise a biologically pure culture of a *Bacillus amyloliquefaciensi* strain Ba-BPD1 (Accession No. DSM 21836), or a mutant thereof having all the identifying characteristics thereof.

In one embodiment, methods are provided for increasing the performance of a monogastric animal comprising: administering to the monogastric animal an effective amount of a feed composition comprising a xylanase enzyme and a biologically pure culture of a *Bacillus licheniformis* strain PWD-1 (Accession No. 53757), or a mutant thereof having all the identifying characteristics thereof. The feed composition may further comprise a biologically pure culture of a *Bacillus amyloliquefaciens* strain Ba-BPD1 (Accession No. DSM 21836), or a mutant thereof having all the identifying characteristics thereof.

In one embodiment, the xylanase is present in the disclosed formulation in an amount ranging from about 10,000-200,000 units/gram. The xylanase can be present in the disclosed formulation in an amount ranging from about 30,000-200,000 units/gram. Thus, the xylanase can be present in an amount of about 10,000; 20,000; 30,000; 40,000; 50,000; 60,000; 70,000; 80,000; 90,000; 100,000; 110,000; 120,000; 130,000; 140,000; 150,000; 160,000; 170,000; 180,000; 190,000; or 200,000 units/gram. One unit of xylanase activity is defined as the amount of enzyme needed for the release of 1 nanomole of reducing sugars (xylose equivalents) per second from 0.5% Xylan (Sima X4252, from Beechwood) at 50° C. in 50 mM trisodium citrate buffer pH 6.0.

In some embodiments, the *Bacillus licheniformis* strain is present in the disclosed formulation in an amount of from about $10^8$ to $10^{12}$ CFU/gram (colony forming units/gram). In some embodiments, the *Bacillus licheniformis* strain is present in the disclosed formulation in an amount of at least about $10^9$ CFU/gram. In some embodiments, the *Bacillus amyloliquefaciens* and *Bacillus licheniformis* strains are present in the disclosed formulation in an amount of from about $10^8$ to $10^{12}$ CFU/gram. In some embodiments, the *Bacillus amyloliquefaciens* and *Bacillus licheniformis* strains are present in the disclosed formulation in an amount of at least about $10^9$ CFU/gram. Thus, the strains can be present in the disclosed formulation in an amount of at least about $10^8$, $10^9$, $10^{10}$, $10^{11}$, $10^{12}$, or $10^{13}$ CFU/gram.

In addition to the xylanase and the bacterial strain(s), the disclosed formulation can further comprise a carrier to improve production, stability, and/or performance characteristics. The term "carrier" as used herein refers to an edible material to which ingredients are added to facilitate uniform incorporation of the ingredients into the disclosed formulation. Suitable carriers can include (but are not limited to) limestone, maltrodextrin, cyclodextrin, wheat, and combinations thereof. In some embodiments, the ratio of active ingredient to carrier can be about 1:9, 1:8, 1:7, 1:6, 1:5, 1:4, 1:3, 1:2, 1:1, 2:1, 3:1, 4:1, 5:1, 6:1, 7:1, 8:1, or 9:1.

The disclosed formulation can be in any desired form, including (but not limited to) a solid, powder, suspension concentration, liquid, or granule.

In some embodiments, the disclosed formulation can be thermally stable to heat treatment up to about 70° C., 80° C., 85° C., 90° C., or 95° C. for a period of up to about 1, 5, 10, 15, 30, or 60 minutes. As used herein, the term "thermally stable" indicates that at least 75% of the components present in the formulation before heating to the specified temperature are still present after it cools to room temperature.

In some embodiments, the disclosed formulation can have a shelf life of greater than 30, 40, 50, 60, 70, or 80 weeks. It should be understood that the desired length of time and normal shelf life can vary upon the storage temperatures, processing conditions, packaging material, packaging equipment, and the like.

The disclosed formulation can be added to a feed composition for consumption by monogastric animals. The formulation can be mixed directly with the animal feed and/or can be mixed with a feed additive (i.e. vitamin feed additive, mineral feed additive, amino acid feed additive, and the like) that is then mixed with the animal feed. Alternatively or in addition, the disclosed formulation can be added to an animal's drinking water.

"Animal feed" or "feed" as used herein refers to any compound, preparation, mixture, or composition suitable for or intended for intake by a monogastric animal. In some embodiments, the feed can comprise a poultry feed or swine feed composition. The term "monogastric animal" as used herein includes any animal with a single stomach and applies to most carnivores and omnivores, with the exception of ruminants. Thus, in some embodiments, suitable monogastric animals can include (but are not limited to) poultry (e.g., broiler chicks, layers, turkeys) and/or swine (e.g., pigs or piglets).

In some embodiments, the disclosed formulation can be added to an animal feed. Thus, the disclosed formulation can be added to animal feed to produce a feed containing a desired amount of xylanase and the disclosed bacterial strain(s). As would be understood to those of ordinary skill in the art, the dilution amount can be determined by the feed needs of the monogastric animal, age of the animal, and intended use (e.g., layers or broilers for chickens). For example, in some embodiments, the concentration of xylanase ranges from about 5 to 30 units/gram feed. In some embodiments, the concentration of xylanase ranges from about 7.5 to 30 units/gram feed (i.e., about 5.0, 5.5, 6.0, 6.5, 7.0, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30 units/gram feed). In some embodiments, the amount of *Bacillus licheniformis* in the feed composition ranges from at least about $5 \times 10^4$ CFU/gram feed. In some embodiments, the amount of *Bacillus licheniformis* in the feed composition ranges from at least about $10^5$ CFU/gram. In some embodiments, the amount of *Bacillus licheniformis* in the feed composition ranges from at least about $10^6$ CFU/gram. In some embodiments, the feed composition further comprises the disclosed *Bacillus amyloliquefaciens* strain at a concentration of at least about $10^5$ CFU/gram feed. In some embodiments, the feed composition comprises a total concentration of both strains of at least about $10^5$ CFU/gram feed. In some embodiments, the feed composition comprises a total concentration of both strains of at least about at least about $2.0 \times 10^5$ CFU/gram.

When administered to a monogastric animal, an effective amount of a feed composition comprising the disclosed formulation has been shown to increase the performance of the animal compared to feed compositions that lack the disclosed formulation. The term "effective amount" refers to the amount of feed sufficient to increase performance in animals without resulting in any significant adverse side effects.

In some embodiments, the increased performance comprises an increased average daily weight gain and/or increased total weight gain in the monogastric animals. The average daily weight gain refers to the total weight gain of all animals over a time period, divided by the total number of animals and the number of days in the period. The total weight gain refers to the entire weight gain of all animals over a time period.

In some embodiments, the increased performance comprises improved feed conversion rate (FCR) of the monogastric animal. Feed conversion rate refers to an animal's efficiency in converting feed mass into increased body mass.

In some embodiments, the increased performance comprises reduced lesion score in the monogastric animal. For example, in some embodiments the animal is poultry and the lesions result from *Clostridium perfringens* or *Eimeria* spp., such as (but not limited to) *Eimeria acervulina, Eimeria tenella,* and/or *Eimeria maxima.*

In some embodiments, the increased performance comprises reduced mortality in the monogastric animal.

In some embodiments, the increased performance comprises reduced disease in the monogastric animal. The pathogens can include (but are not limited to) *Clostridium perfringens, Eimeria* spp., *Eimeria acervulina, Eimeria tenella, Eimeria maxima,* and/or Coccidiosis-inducing parasites. One or both of the disease and lesion score can be a result of one or a combination of *Clostridium perfringens, Eimeria acervulina, Eimeria tenella, Eimeria maxima,* or Coccidiosis-inducing parasites.

In some embodiments, the increased performance comprises decreased pathogen incidence. In some embodiments, incidence of pathogens is reduced in the animal's production environment (i.e., floor pen litter) and/or in the intestines of the animal. In one embodiment, the animal may be poultry and the increase in performance comprises reduced lesion score resulting from one or a combination of *Clostridium perfringens* or *Eimeria* spc. In another embodiment, the animal is poultry and the decreased pathogen incidence is a decreased *Salmonella* incidence.

EXAMPLES

The following EXAMPLEs have been included to provide guidance to one of ordinary skill in the art for practicing representative embodiments of the presently disclosed subject matter. In light of the present invention and the general level of skill in the art, those of skill can appreciate that the following EXAMPLEs are intended to be exemplary only and that numerous changes, modifications, and alterations can be employed without departing from the scope of the presently disclosed subject matter.

Example 1

Assessment of *B. licheniformis* Strain PWD-1 Probiotic Characteristic In Vitro

*B. licheniformis* strain PWD-1 was tested against the pathogen surrogates *E. coli, Salmonella enterica, Listeria innocua,* and *Campylobacter hyointestinalis* via a series of agar well diffusion assays. In each assay, one of the pathogen surrogates was spread onto 3 agar plates and *B. licheniformis* strain PWD-1 was put into the well of each plate. The plates were then incubated overnight at 37° C. and photographed to show the interaction between the pathogens and the *B. licheniformis.*

FIGS. 1a and 1b illustrate that *B. licheniformis* strain PWD-1 overgrows *Listeria innocua* and *Salmonella enteria,* respectively.

Example 2

Assessment of *B. amyloliquefaciens* strain Ba-BPD1 Probiotic Characteristic In Vitro The experiment of Example 1 was repeated using *B. amyloliquefaciens* strain Ba-BPD1 in place of *B. licheniformis* strain PWD-1.

FIGS. 2a and 2b illustrate that *B. amyloliquefaciens* strain Ba-BPD1 inhibits the growth of *E. coli* and *Salmonella enterica,* respectively. FIG. 2c illustrates that *B. amyloliquefaciens* strain Ba-BPD1 outgrows *Listeria innocua.*

Example 3

Acid Resistance Study of *B. licheniformis* Strain PWD-1 and *B. amyloliquefaciens* Strain Ba-BPD1

The resistance of probiotic microorganisms to acidic environments is an important feature due to exposure of the probiotic to the harsh acidic conditions present in the gut of an animal before passing into the intestine. *B. licheniformis* strain PWD-1 was subjected to LB media at pH 3.0 for time points of 0, 1, 2, and 3 hours. The media was then neutralized to pH 7.0 and growth was monitored by absorbance at 600 nm. The experiment was repeated for *B. amyloliquefaciens* strain Ba-BPD1.

As shown in FIG. 3a, the exposure of *B. licheniformis* strain PWD-1 to an acidic environment delayed growth for 3 hours compared to neutral media. It was also observed that *B. licheniformis* strain PWD-1 exposed to the acidic environment for 1, 2, and 3 hours was able to recover and assume growth. As shown in FIG. 3b, *B. amyloliquefaciens* strain Ba-BPD1 was also able to recover from the acid exposure, although slower than observed for the *B. licheniformis* strain.

Example 4

Bile Resistance Study of *B. licheniformis* Strain PWD-1 and *B. amyloliquefaciens* Strain Ba-BPD1

The survival of probiotic microorganisms in a gastric environment includes not only a low pH environment, but also enzymes secreted into the gastrointestinal tract. Traditionally, Ox gall (cow gall mixed with alcohol) has been used as a representation of the gastric environment. *B. licheniformis* strain PWD-1 was exposed to 0.3% Ox gall in LB media for 0, 1, 2, or 3 hours and growth was monitored for 8 hours by absorbance at 600 nm, as shown in FIG. 4a. The experiment was repeated for *B. amyloliquefaciens* strain Ba-BPD1, as shown in FIG. 4b.

The figures illustrate that both *B. licheniformis* strain PWD-1 and *B. amyloliquefacienis* strain Ba-BPD1 were able to recover after up to 3 hours of exposure to Ox gall in LB media.

Example 5

Adherence of *B. licheniformis* Strain PWD-1 and *B. amyloliquefaciens* Strain Ba-BPD1 to Intestinal Mucus Attachment of probiotic strains to intestinal mucus is desirable because it limits access of pathogens to the mucus lining. *B. licheniformis* strain PWD-1 and *B. amyloliquefaciens* strain Ba-BPD1 were tested to assess the ability to attach to swine mucus. Controls *B. subtilis* strain 168-a from ATCC and *B. subtilis* strain C102 of Calsporin were also tested. No protein coating (buffer only) and BSA (bovine serum albumin) were used as controls. Growth of each strain was monitored, as shown in FIG. 5. The graphs show that *B. licheniformis* strain PWD-1 adheres to swine mucus at comparable levels to strain *B. subtilis* strain C102.

Example 6

Investigation of the Effects of the Addition of Xylanase and *B. licheniformis* Strain PWD-1 to the Diet of Commercial Broilers Subjects: Day-old, mixed sex, Ross 708 broilers.

Statistical Design: Randomized complete block design (RCBD).

Treatments: 2×2 factorial arrangement with xylanase (XYLAMAX, available from BioResource International, Inc., Durham, N.C., United States) and *B. licheniformis* strain PWD-1 ("ProB") as two factors, as set forth in Table 1 below.

TABLE 1

| | Treatments | |
|---|---|---|
| Treatment | Xylanase (U/g feed) | Pro B (CFU/g feed) |
| Control | 0 | 0 |
| Pro B | 0 | $10^6$ |
| Xylanase | 15 | 0 |
| Pro B + Xylanase | 15 | $10^6$ |

Duration: 0-42 days.

Replication: 52 birds per pen and 8 pens per treatment.

Diets: All treatments included 3 phases of diets (i.e., starter, grower, and finisher), as set forth in Table 2 below. Each diet was corn/soy-based, but had 100 kcal/kg less metabolizable energy (ME) compared to a standard broiler diet.

TABLE 2

| Animal Diet Summary | | | |
|---|---|---|---|
| Phase | Age (days) | ME (Kcal/kg) | Crude Protein (%) |
| Starter | 0-21 | 2930 | 22 |
| Grower | 22-35 | 3030 | 20 |
| Finisher | 36-42 | 3080 | 19 |

Disease Challenges: Built-up litter was used to create a "mild field-like, subclinical challenge model" in the study. Bacteria included *Clostridium perfringens, Eimeria acervulina*, and *Eimeria maxima*.

Response Measures: Set forth in Table 3, below. Group BWG (body weight gain) and FCR (feed conversion ratio) for various periods were calculated based on BW (body weight) and FI (food intake).

TABLE 3

| Response Measures | |
|---|---|
| Response | Data Collection |
| BW (individual) | Days 0, 14, 21, 42 |
| FI (pen) | Days 0, 14, 21, 42 |
| Mortality | As occurred |
| Lesion Score | Days 14, 21, 42 |
| *Salmonella* incidence | Days 21, 42 |

Statistical Methods: Analyzed by ANOVA (analysis of variance) and LSD (least significant difference). The difference was considered significant if $p<0.05$.

Results: As shown in FIG. 6, xylanase significantly ($p<0.05$) reduced lesion score at 14-days, 21-days, and 42-days of age, and that *B. licheniformis* strain PWD-1 significantly ($p<0.05$) reduced lesion score at 14-days and 21-days of age. The improvement of the xylanase and *B. licheniformis* strain PWD-1 combination was shown to be greater than either component alone. Particularly, at 21 and 42 days, the effect of combining xylanase and *B. licheniformis* strain PWD-1 was greater than the sum of either component alone, illustrating a synergistic effect (see also Table 4 below, * indicates a strong synergistic effect). At the 42 day time point, the improvement due to the combination feed was pronounced at greater than twice that of each component alone. Thus, the combination of the xylanase and the *B. licheniformis* Strain PWD-1 shows synergistic improvements in animal health.

TABLE 4

Number of intestinal lesion scores in broilers challenged with *Clostridium perfringens*, *Eimeria acervulina*, and *Eimeria maxima* and fed a feed composition containing $10^6$ CFU/g *B. licheniformis* Strain PWD-1 and 15 U/g xylanase.

| | Lesion Scores | | | | | | | |
|---|---|---|---|---|---|---|---|---|
| Age (Days) | Control | Pro B | Xylanase | Combined Pro B/ Xylanase | Reduction Pro B alone | Reduction Xylanase alone | Reduction Pro B/ Xylanase combined | Calculated Additive Reduction Pro B and Xylanase Separately |
| 14 | 1.63 | 1.00 | 0.50 | 0.25 | −(0.63) | −(1.13) | −(1.38) | −(1.73) |
| 21 | 1.28 | 1.03 | 0.94 | 0.38 | −(0.25) | −(0.34) | −(0.90*) | −(0.59) |
| 42 | 1.21 | 1.06 | 1.03 | 0.43 | −(0.15) | −(0.18) | −(0.78*) | −(0.33) |

FIGS. 7a and 7b illustrate that xylanase and *B. licheniformis* strain PWD-1 significantly (p<0.05) improved BW of the birds at 21-days and 42-days of age. In addition, the improvement of the xylanase and *B. licheniformis* strain PWD-1 combination was shown to be greater than either component alone.

The results further illustrate that xylanase and *B. licheniformis* strain PWD-1 significantly (p<0.05) improved FCR at 21-days and 42-days of age (FIGS. 8a and 8b). In addition, the improvement of the xylanase and *B. licheniformis* strain PWD-1 combination was greater than either component alone, as shown in FIGS. 8a and 8b.

FIGS. 9a and 9b illustrate that xylanase and *B. licheniformis* strain PWD-1 significantly (p<0.05) reduced *Salmonella* incidence at 21-days and 42-days of age. In addition, the improvement of the xylanase and *B. licheniformis* strain PWD-1 combination was greater than either component alone.

Conclusions: Xylanase and *B. licheniformis* strain PWD-1, when added in combination to a corn/soy diet, significantly improved broiler growth performance and gut health under *Clostridium perfringens* and multiple *Eimeria* species challenges. The data support the conclusion that the effects of the combination of xylanase and *Bacillus licheniformis* strain PWD-1 include synergistic beneficial effects on animal health.

Example 7

Investigation of the Effects of the Addition of Xylanase, *B. licheniformis* Strain PWD-1, and *B. amyloliquefaciens* Strain Ba-BPD1 to the Diet of Commercial Broilers Subjects: Day-old, mixed sex, Ross 708 broilers.
Statistical Design: Randomized complete block design (RCBD).
Treatments: Six treatments with xylanase (xyl, available from BioResource International, Inc., Durham, N.C., United States), *B. licheniformis* strain PWD-1 (ProB), and *B. amyloliquefaciens* strain Ba-BPD1 (ProY), and antibiotic BMD (bacitracin methylene disalicylate) as variables, as set forth in Table 5.

TABLE 5

| | Treatments | | | |
|---|---|---|---|---|
| Treatment | Xylanase (U/g feed) | ProB (CFU/g feed) | ProY (CFU/g feed) | BMD (g/ton of feed) |
| Control | 0 | 0 | 0 | 0 |
| Xyl + B5 + Y5 | 15 | $10^5$ | $10^5$ | 0 |
| Xyl + B6 + Y6 | 15 | $10^6$ | $10^6$ | 0 |
| Xyl + B6 + Y4 | 15 | $10^6$ | $10^4$ | 0 |
| Xyl + B4 + Y6 | 15 | $10^4$ | $10^6$ | 0 |
| AGP | 0 | 0 | 0 | 50 |

Duration: 0-42 days.
Replication: 52 birds per pen and 10 or 6 pens per treatment.
Diets: All treatments included 3 phases of diets (i.e., starter, grower, and finisher), as set forth in Table 5 above. Each diet was corn/soy-based, but had 100 kcal/kg less metabolizable energy (ME) compared to a standard broiler diet.
Disease Challenges: Built-up litter was used to create a "mild field-like, subclinical challenge model" in the study. Bacteria included *Clostridium perfringens*, *Eimeria acervulina*, and *Eimeria maxima*, and *Eimeria tenella*.

Response Measures: As set forth in Table 5 above, group BWG (body weight gain) and FCR (feed conversion ratio) for various periods were calculated based on BW (body weight) and FI (food intake).

Statistical Methods: Data were analyzed by ANOVA and LSD. The difference was considered significant if p<0.05.

Results: As shown in FIG. 10, supplementing feed with xylanase and *Bacillus* strains (*Bacillus licheniformis* strain PWD-1 and *Bacillus amyloliquefaciens* strain Ba-BPD1) at $2 \times 10^5$ CFU/g of feed or higher significantly (p<0.05) improved body weight at 21-days of age.

As shown in FIGS. 11a and 11b, supplementing feed with xylanase and *Bacillus* strains (*Bacillus licheniformis* strain PWD-1 and *Bacillus amyloliquefaciens* strain Ba-BPD1) at $2 \times 10^5$ CFU/g of feed or higher significantly (p<0.05) improved FCR at 21-days and 42-days of age.

Further, FIGS. 12a and 12b illustrate that supplementing feed with xylanase and *Bacillus licheniformis* strain PWD-1 and *Bacillus amyloliquefaciens* strain Ba-BPD1 at $2 \times 10^5$ CFU/g of feed or higher significantly (p<0.05) reduced mortality of the birds at 21-days and 42-days of age (mortality was reduced by 80% on average at 42 days). In contrast, AGP (BMD) inclusion did not significantly improve mortality from the control.

Conclusion: Xylanase combined with *Bacillus licheniformis* strain PWD-1 and *Bacillus amyloliquefaciens* strain Ba-BPD1, when added to a corn/soy diet, significantly improved broiler growth performance under *Clostridium perfringens* and multiple *Eimeria* species challenges. The data supports the conclusion that combining *Bacillus licheniformis* strain PWD-1 and *Bacillus amyloliquefaciens* strain Ba-BPD1 with xylanase is effective at various inclusion levels ($10^5$ to $10^6$ CFU/g of feed).

Example 8

Effect of the Addition of Xylanase, *B. licheniformis* Strain PWD-1, and *B. amyloliquefaciens* Strain Ba-BPD1 to the Diet of Commercial Broilers Under Severe Coccidiosis Challenge Conditions The objective of this study was to evaluate the efficacy of 100 g/Metric Ton inclusion of a combination of xylanase (10 U/g feed), *B. licheniformis* strain PWD-1 ($1 \times 10^5$ CFU/g feed), and *B. amyloliquefaciens* strain Ba-BPD1 ($5 \times 10^5$ CFU/g feed), to minimize the severity of gut lesions and improve overall livability of broiler chickens fed standard corn-soy diets and reared under severe coccidiosis challenge conditions.

MATERIALS AND METHODS: Four hundred male Ross 708 broiler chicks were randomly assigned to 1 of 4 dietary treatments, with 7 replicate battery cages per treatment (except Treatment 1, the unchallenged positive control, which contained 4 replicate cages), and 16 birds per cage. Birds were reared for 28 days and fed mash, corn-soy-based diets ad libitum. Birds of Treatments 2-4 were twice challenged with a live vaccine containing the live oocysts of highly-immunogenic, coccidiostat-sensitive strains of *Eimeria acervulina*, *Eimeria maxima* and *Eimeria tenella* by oral gavage, at a rate of 1 mL/bird (10× the vaccine manufacturer's recommended dose). Birds of Treatment 1, the unchallenged positive control, were gavaged with 1 mL/bird distilled water. Oral gavages were performed at both 1 and 7 days of age, in all treatment groups. In Treatments 3 and 4, feed was supplemented with either xylanase (10 U/g feed), *B. licheniformis* strain PWD-1 (1×10$^5$ CFU/g feed), and *B. amyloliquefaciens* strain Ba-BPD1 (5×10$^5$ CFU/g feed) referred to as "Xyl+B+Y" or a commercial coccidiostat (salinomycin sodium) referred to as "Coccidiostat". The key parameters evaluated were upper-tract intestinal lesion scores, middle-tract intestinal lesion scores, mortality/livability, and feed conversion ratio (FCR).

RESULTS AND DISCUSSION: Cocci-linked gross lesions of the upper intestines are closely associated with *E. acervulina* infections and are often most severe within 7 days of initial infection. At 7 days post-challenge (14 days of age), Xyl+B+Y alone reduced upper-tract lesion scores by 36%, relative to the challenged control (data not shown).

The mid-section of the intestines (comprised of the ileum and portions of the duodenum and jejunum) is most susceptible to *E. maxima* infections. At 14 days post-challenge, Xyl+B+Y alone reduced mid-tract lesion scores by 50%, compared to the challenged control (data not shown).

Figure 13:
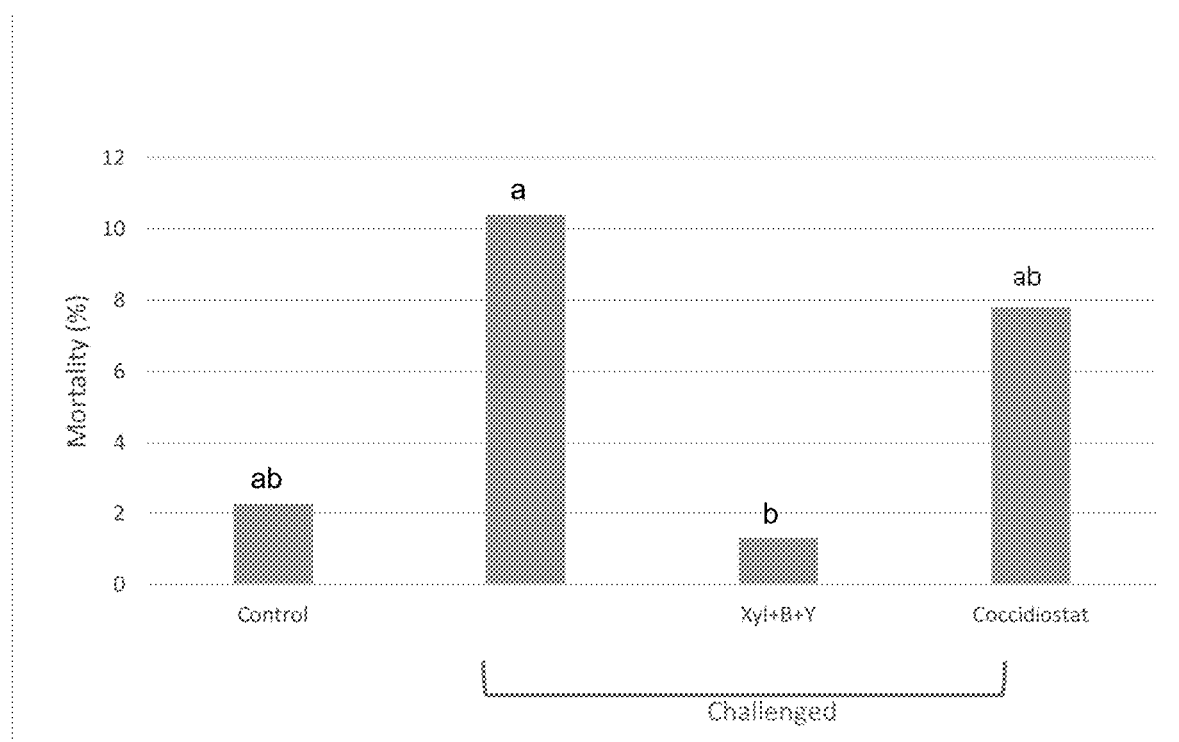
FIG. 13 is a bar graph illustrating the mortality of 28-day old broilers fed animal feed supplemented with either a combination of xylanase (10 U/g feed), *B. licheniformis* strain PWD-1 ($1\times10^5$ CFU/g feed), and *B. amyloliquefaciens* strain Ba-BPD1 ($5\times10^5$ CFU/g feed) ("Xyl+B+Y") or salinomycin sodium ("Coccidiostat") after challenge with coccidiostat-sensitive strains of *Eimeria acervulina*, *Eimeria maxima* and *Eimeria tenella* by oral gavage relative to control and unchallenged broilers.

The *Eimeria* challenge regimen performed in the current study resulted in significant increase (P<0.02) in 28-day mortality of the challenged control group, compared the unchallenged control. The data are shown in FIG. 13. However, mortality was significantly reduced (P<0.02) in the Xyl+B+Y treatment by 87%, compared to the challenged control. Comparatively the Coccidiostat treatment only reduced mortality by 25%.

At 28 days, feed conversion ratio was reduced in the Xyl+B+Y treatment by 7 points, versus the challenged control. Day 28 body weight was not affected by treatment and averaged 1226 g/bird, across treatments (data not shown).

In conclusion, under conditions of severe coccidiosis, the combination of the xylanase (10 U/g feed), *B. licheniformis* strain PWD-1 (1×10$^5$ CFU/g feed), and *B. amyloliquefaciens* strain Ba-BPD1 (5×10$^5$ CFU/g feed) alone can effectively protect the gut health of broilers by reducing the severity of intestinal lesions, thereby maintaining gut function and promoting strong utilization of nutrients. This combination of xylanase, *B. licheniformis* strain PWD-1, and *B. amyloliquefaciens* strain Ba-BPD1 can be more effective than coccidiostat alone at minimizing mortality of birds suffering severe *Eimeria* infections.

What is claimed is:

1. A method for increasing the performance of poultry, wherein increasing performance comprises one or more of improved feed conversion rate or reduced lesion score, comprising: administering to the poultry a feed composition comprising an endo-1,4-beta-xylanase enzyme in an amount of 10-15 units/gram feed and a biologically pure culture of a *Bacillus licheniformis* strain PWD-1 (Accession No. 53757) in an amount of 10$^5$ CFU/gram feed to 10$^6$ CFU/gram feed.

2. The method of claim 1, wherein the poultry is a broiler.

3. The method of claim 1, wherein the lesion score is a result of one or a combination of *Clostridium perfringens, Eimeria acervulina, Eimeria maxima, Eimeria tenella* or Coccidiosis-inducing parasites.

4. The method of claim 1, wherein the increase in performance comprises reduced lesion score resulting from one or a combination of *Clostridium perfringens* or *Eimeria* spc.

5. A method for increasing the performance of poultry, wherein increasing performance comprises one or a combination of: increased total weight gain, improved feed conversion rate, or reduced mortality, comprising: administering to the poultry a feed composition comprising an endo-1,4-beta-xylanase enzyme in an amount of 10-15 units/gram feed, a biologically pure culture of a *Bacillus licheniformis* strain PWD-1 (Accession No. 53757) in an amount of 10$^5$ CFU/gram feed to 10$^6$ CFU/gram feed, and a biologically pure culture of a *Bacillus amyloliquefaciens* strain Ba-BPD1 (Accession No. DSM 21836) in an amount of 10$^5$ CFU/gram feed to 10$^6$ CFU/gram feed.

6. The method of claim 5, wherein the poultry has a disease challenge as a result of one or a combination of *C. perfringens, E. acervulina*, and *E. maxima*.

\* \* \* \* \*